(12) United States Patent
Quellet

(10) Patent No.: US 12,251,454 B2
(45) Date of Patent: Mar. 18, 2025

(54) PERFUME COMPOSITIONS

(71) Applicant: GIVAUDAN SA, Vernier (CH)

(72) Inventor: Christian Quellet, Bienne (CH)

(73) Assignee: GIVAUDAN SA, Vernier (CH)

( * ) Notice: Subject to any disclaimer, the term of this patent is extended or adjusted under 35 U.S.C. 154(b) by 0 days.

(21) Appl. No.: 18/474,782

(22) Filed: Sep. 26, 2023

(65) Prior Publication Data

US 2024/0016711 A1    Jan. 18, 2024

Related U.S. Application Data

(63) Continuation of application No. 16/349,513, filed as application No. PCT/EP2017/083211 on Dec. 18, 2017, now abandoned.

(30) Foreign Application Priority Data

Dec. 21, 2016    (GB) ...................... 1621887

(51) Int. Cl.
| | |
|---|---|
| *A61K 8/11* | (2006.01) |
| *A61K 8/34* | (2006.01) |
| *A61K 8/35* | (2006.01) |
| *A61Q 13/00* | (2006.01) |
| *A61Q 15/00* | (2006.01) |

(52) U.S. Cl.
CPC ............... *A61K 8/11* (2013.01); *A61K 8/34* (2013.01); *A61K 8/35* (2013.01); *A61Q 13/00* (2013.01); *A61Q 15/00* (2013.01); *A61K 2800/412* (2013.01)

(58) Field of Classification Search
CPC .......... A61K 8/11; A61K 8/34; A61K 8/35; A61K 2800/412; A61Q 13/00; A61Q 15/00
See application file for complete search history.

(56) References Cited

U.S. PATENT DOCUMENTS

| | | | | |
|---|---|---|---|---|
| 7,012,053 | B1 * | 3/2006 | Barnabas | C11D 3/373 510/276 |
| 7,071,157 | B2 * | 7/2006 | Santos | C11D 3/001 510/516 |
| 2002/0037817 | A1 | 3/2002 | Foley et al. | |
| 2008/0176780 | A1 * | 7/2008 | Warr | D06M 13/005 510/103 |
| 2012/0058929 | A1 | 3/2012 | Laubender et al. | |
| 2014/0017287 | A1 * | 1/2014 | Lei | A61K 8/34 264/4.1 |
| 2015/0259629 | A1 | 9/2015 | Jones et al. | |
| 2017/0017214 | A1 | 1/2017 | O'Keeffe | |

FOREIGN PATENT DOCUMENTS

| | | | | |
|---|---|---|---|---|
| EP | 1894603 A1 | 3/2008 | | |
| JP | 2016530982 A | 10/2016 | | |
| JP | 2016534159 A | 11/2016 | | |
| WO | 2004016234 A1 | 2/2004 | | |
| WO | 2006095200 A1 | 9/2006 | | |
| WO | 2008098387 A1 | 8/2008 | | |
| WO | 2009100553 A1 | 8/2009 | | |
| WO | 2015/016367 A1 | 2/2015 | | |
| WO | 2015/016368 A1 | 2/2015 | | |
| WO | WO-2015110568 A1 * | 7/2015 | | B01J 13/14 |

OTHER PUBLICATIONS

Creating Perfume, Tetrahydrolinaolool, Jan. 22, 2015, p. 102 (Year: 2015).*
Elsharif et al., "Structure-odor relationships of linalool, linalyl acetate and their corresponding oxygenated derivatives", Frontiers in Chemistry, Volume, Article 57, Oct. 2015. (Year: 2015).*
International Search Report and Written Opinion of the International Searching Authority for corresponding application PCT/EP2017/083211 dated Feb. 5, 2018.
GB Search Report for corresponding application GB 1621887.7 dated Oct. 11, 2017.

* cited by examiner

*Primary Examiner* — Jianfeng Song
(74) *Attorney, Agent, or Firm* — Norris McLaughlin, PA

(57) ABSTRACT

Disclosed are encapsulated perfume compositions showing improved balance between storage stability in consumer products and perfume diffusivity from intact microcapsules deposited on substrates (so-called pre-rub performance), the compositions comprising a combination of long chain aldehydes having 10 carbon atoms or more and/or tertiary alcohols having 10 carbon atoms or more, in combination with blooming perfume ingredients.

17 Claims, No Drawings

PERFUME COMPOSITIONS

This is a continuation application of U.S. Ser. No. 16/349,513, filed 13 May 2019, which in turn was an application filed under 35 USC 371 based on PCT/EP2017/083211, filed 18 Dec. 2017, which in turn is based on GB 1621887.7 filed 21 Dec. 2016. The present application claims the full priority benefit of these prior applications and herein incorporates by reference the full disclosures of these prior applications

FIELD OF THE INVENTION

The present disclosure relates to encapsulated perfume compositions in core-shell microcapsules providing suitable balance between pre-rub performance and stability during storage in consumer products. More particularly, the present disclosure relates to products comprising said core-shell microcapsules for use in laundry care, home care, hair care and body care. The present disclosure also relates also to method of selecting perfume ingredients, based on synergistic optimization, in order to provide said encapsulated perfume compositions.

BACKGROUND OF THE INVENTION

Consumer products, such as detergents, shampoos and conditioners typically contain perfumes that are expected to deliver long-lasting and pleasant odours to substrates onto which they are applied. However, it is often not possible to achieve this goal if perfumes are incorporated into such products in neat form, as so-called "free-oil". For this reason, it is common to formulate perfume compositions in the cores of core-shell microcapsules.

The advantages of encapsulating perfumes in this way are well known in the art. In particular, microcapsules can increase the stability and useful life of the encapsulated perfume ingredients; they can facilitate the manipulation, handling and storage of the encapsulated perfume compositions, and control the emanation of pleasant odours in time and space; and they can also isolate perfume ingredients from chemical attack of aggressive external media in which they are suspended.

However, it remains a matter of considerable difficulty for formulators to design core-shell microcapsules that possess the requisite barrier properties to protect the core contents from external media during manufacture and storage, and yet still permit release of the core contents at a desired time, in response to an external stimulus, such as the action of heat, moisture, chemical reactivity, or in response to mechanical disruption.

Core-shell microcapsules, particularly those comprising aminoplast resins, are somewhat permeable to their core contents when suspended in certain media, such as aqueous media, and particularly aqueous media containing surfactants. Perfume ingredients tend to be extracted from the cores over time in a process of diffusion. This is particularly a problem in media containing unstructured surfactants, which promote this process by solubilizing or incorporating perfume ingredients into micelles. It is obviously not desired that the core contents are extracted prematurely, but at the same time the shells should not present such a tough barrier that the microcapsules cannot be persuaded to deliver up their contents other than with the application of excessive physical force applied to a substrate on which the microcapsules are deposited.

Today's consumers increasingly measure the efficacy of a fragranced consumer product not only in terms of the perfume intensity in response physical force being applied to a dry treated substrate, such as skin, hair or fabrics (the so-called post-rub intensity), but also the fragrance perception on wet substrates (pre-rub intensity). Post-rub intensity might be desirable for sustained perfume benefits, but up-front freshness and perfume intensity before rubbing is also desirable to ensure perfume benefits are perceivable at all stages of application of a consumer product. For example, an intense and diffusive smell may be desired on opening a wash machine after laundry washing or during drying in a tumbler or line drying.

The prior art has attempted to address perfume benefits in encapsulated perfume compositions by proposing rules for the selection of perfume ingredients. For example, improved perfume delivery from capsules has been claimed for perfumes comprising large amounts of ingredients having high clogP values as illustrated in U.S. Pat. No. 5,500,138.

WO2004/016234 A1 suggests perfume ingredients having clog P values of 2.5 or greater should be used in high amounts, i.e. 80-90% by weight, for optimal performance.

In EP 1 533 364 A2 clogP is regarded as a key parameter in encapsulated perfume design. Preferred perfume ingredients should have clogP values of 3.3 or greater, more particularly 4 or greater and that these ingredients should be used in high amounts, for example greater than 80%, more particularly greater than 90% by weight.

The applicant has found, however, that selecting perfume ingredients suitable for encapsulation based on a consideration of their clogP values neither accounts adequately for the leakage stability of microcapsules when suspended in media containing high levels of surfactants, nor for pre-rub perfume impact of said encapsulated perfume compositions.

There is therefore a need to for encapsulated perfume compositions that are resistant to leakage during storage in consumer product bases, particularly in products containing high levels of surfactants and/or solvents, and that exhibit intense and diffusive pre-rub odour impact once deposited on a substrate.

SUMMARY OF THE INVENTION

The present invention relates to encapsulated perfume compositions in core-shell microcapsule that are particularly stable with respect to the leakage of encapsulated blooming, diffusive fragrances, so that the level of such fragrances in the microcapsules is still sufficiently high after storage in products, to provide enhanced pre-rub odour impact.

In a first aspect of the invention, an encapsulated perfume composition is provided in the form of plurality of core-shell microcapsules, characterized in such that:
   a) the microcapsule shell thickness is lower than 0.5 µm, preferably lower than 0.3 µm, for example 0.25 µm; and
   b) the encapsulated perfume composition must comprise:
      i. from 5 to 35% by weight of GROUP A perfume ingredients selected from long chain aldehydes having 10 carbon atoms or more, preferably 11 carbon atoms or more, and most preferably 12 carbon atoms or more; and/or tertiary alcohols having 10 carbon atoms or more; and
      ii. from 5 to 25% by weight of GROUP B blooming perfume ingredients, selected from the group consisting of hexan-1-aol (for example ALDEHYDE C 6 HEXYLIC FOOD GRADE); heptanal (for example ALDEHYDE C 7 HEPTYLIC); 2-(2-mercaptopropan-2-yl)-5-methylcyclohexanone (for example CORPS CASSIS); (E)-1-(2,6,6-trimethylcyclohexa-1,3-dien-1-yl)but-2-en-1-one (for example DAMASCENONE); (E)-1-(2,6,6-trimethylcyclohex-3-en-1-yl)but-2-en-1-one (for example DAMASCONE DELT); (E)-dec-4-enal (for example DECENAL-4-TRANS); 1-methoxy-4-propylbenzene (for example DIHYDRO ANETHOLE); ethyl butanoate (for example ETHYL BUTYRATE); ethyl butanoate (for example ETHYL BUTYRATE); ethyl hexanoate (for example ETHYL CAPROATE); ethyl 2-methylpropionate (for example ETHYL ISOBUTYRATE); ethyl 3-methylbutanoate (for example ETHYL ISOVALERAT); ethyl 2-methylbutanoate (for example ETHYL METHYL-2-BUTYRATE); ethyl 2,6,6-trimethylcyclohexa-1,3-diene-1-carboxylate (for example ETHYL SAFRANATE); (1S, 4S)-1,3,3-trimethyl-2-oxabicyclo[2.2.2]octane (for example EUCALYP); methyl oct-2-ynoate (for example FOLIONE); 2-methoxyphenol (for example GUAIA); ethyl 2-methylpentanoate (for example MANZANAT); 2,6-dimethylhept-5-enal (for example MELONAL); methyl 2-hydroxy-5-methylbenzoate (for example METHYL CRESOTATE PARA); methyl 2-methylbutanoate (for example METHYL METHYL BUTYRATE); (2E,6Z)-nona-2,6-dienal (for example NONADIENAL); (2E,6Z)-nona-2,6-dien-1-ol (for example NONADIENOL-2,6); (Z)-non-6-enal (for example NONENAL-6-CIS); 2-phenyl-ethanal (for example PHENYL ACETALDEHYDE); (2E,5E)-5,6,7-trimethylocta-2,5-dien-4-one (for example POMAROS); 4-methyl-2-(2-methylprop-1-en-1-yl) tetrahydro-2H-pyran (for example ROSE OXIDE C); 2,6,6-trimethylcyclohexa-1,3-dienecarbaldehyde (for example SAFRANAL); 4-vinylcyclohex-1-enecarbaldehyde (for example SHISOLIA); 4-methylbenzaldehyde (for example TOLYL ALDEHYDE PARA EXTRA); 2-ethoxy-4-methylphenol (for example ULTRAVANIL); (3E,5Z)-undeca-1,3,5-triene (for example UNDECATRIENE); (2E,6Z)-nona-2,6-dienenitrile (for example VIOLET NITRILE); and ethyl cyclohexanecarboxylate; and wherein the relative concentration ranges of GROUP A ingredients and of GROUP B are selected in the a way that when the level of GROUP A is from 5 to 10 wt %, then the level of GROUP B ingredients must be from 10 to 25 wt %; when the level if GROUP A is between 10 and 30 wt %, then the level of GROUP B ingredients must be from 5 to 25 wt %; when the level of GROUP B ingredients is from 5 to 10 wt %, then the level of GROUP A ingredients must be between 10 and 30 wt %; and when the level of GROUP B ingredients is between 10 and 25 wt %, then the GROUP A ingredients must be from 5 to 30 wt %.

In another aspect of the invention, is provided a method for enhancing the pre-rub performance of encapsulated perfume compositions, by mixing blooming ingredients with long chain aldehydes having 10 carbon atoms or more, preferably 11 carbon atoms or more, and most preferably 12 carbon atoms or more; and/or tertiary alcohols having 10 carbon atoms or more.

In another aspect of the invention, the use of long chain aldehydes having 10 carbon atoms or more, preferably 11 carbon atoms or more, and most preferably 12 carbon atoms or more; and/or tertiary alcohols having 10 carbon atoms or more, for enhancing the blooming performance of encapsulated perfume compositions.

In another aspect are provided consumer products, comprising the encapsulated perfume compositions of the invention.

DETAILED DESCRIPTION OF THE INVENTION

In order to deliver optimal performance in terms of perfume release, the shell of core-shell microcapsules used in consumer products must be as thin as possible, in particular below 0.5 micrometre (μm), more particularly below 0.3 μm. Microcapsules having such thin shells are indeed more prone to mechanical rupture. They are also more suitable for passive diffusion of blooming ingredients in the pre-rub state.

Under "pre-rub performance" is meant the property of a microcapsule to provide an intense and diffusive odour, on wet substrates. Such an intense and diffusive may, for example, perceived when opening a laundry wash machine or a tumble dryer, or after having sprayed a suspension of microcapsules on a substrate. The pre-rub performance may be assessed by panellists. For example, the towels are carefully removed from the wash machine and the olfactive assessment is performed by sniffing the wet towels, without handling them with hands or any other instrument.

The perfume ingredients which are responsible for the intense and diffusive odour of a perfume are often called blooming ingredients have moderate to high vapour pressures, for example higher than 0.2 mmHg at 25° C., and are particularly powerful in terms of odour strength. As described in more details hereinafter, the odour strength is related to the so-called odour value of the perfume ingredient.

However, thin shells make the microcapsules also more permeable and less stable with respect to diffusion of blooming ingredients during prolonged storage times in products, compared to thick shells.

The applicant has now discovered that, in order to exhibit an intense and diffusive pre-rub odour impact in the pre-rubbed state (also referred hereafter as pre-rub performance), while still being resistant to leakage in product bases containing high levels of surfactants, an encapsulated perfume composition must obey different composition patterns than those set forward by the prior art.

In particular, the applicant has discovered that, in order to obtain encapsulated perfume compositions that exhibit such pre-rub odour performance and storage stability,
1. the microcapsule shell thickness must be lower than 0.5 μm, preferably lower than μm, for example 0.25 μm; and
2. the encapsulated perfume composition must comprise:
   I. from 5 to 35% by weight of GROUP A perfume ingredients selected from long chain aldehydes having 10 carbon atoms or more, preferably 11 carbon atoms or more, and most preferably 12 carbon atoms or more; and/or tertiary alcohols having 10 carbon atoms or more; and
   II. from 5 to 25% by weight of GROUP B blooming perfume ingredients;
   wherein the relative concentration ranges of GROUP A ingredients and of GROUP B ingredients are selected in such a way that when the level of GROUP A is from 5 to 10 wt %, then the level of GROUP B ingredients must be from 10 to 25 wt %; when the level if GROUP A is between 10 and 30 wt %, then the level of GROUP B ingredients must be from 5 to 25 wt %; when the level of GROUP B ingredients is from 5 to 10 wt %, then the level of GROUP A ingredients must be between 10 and 30 wt %; and when the level of GROUP B ingredients is between 10 and 25 wt %, then the GROUP A ingredients must be from 5 to 30 wt %.

The use of the term "storage stability" refers to the capability of a microcapsule to be sufficiently impervious to avoid loss of pre-rub performance when stored in product bases containing high level of surfactants and solvents, for example more than 5% by weight, more particularly more than 15% by weight, still more particularly more than 25% by weight of surfactant or solvents. Typically, in a storage stability test, the product containing the microcapsules is stored for one to three months at a temperature of from 35 to 50° C.

The term "blooming ingredient" as used herein, refers to those blooming ingredients referred to herein above, and more generally those perfume ingredients having a vapour pressure higher than 0.02 mmHg at 25° C. and/or an Odour Value (OV) higher than $10^6$.

The "odour value" (OV) of a perfume ingredient is defined as the ratio of the standard equilibrium headspace concentration (HS), expressed in microgram/L/the odour detection threshold (ODT), also expressed in microgram/L.

The term "$\log_{10}OV$", also referred to as log(OV) hereafter, refers to the common (or decimal) logarithm of odour value defined above.

The standard equilibrium headspace concentration (HS), expressed in microgram/liter (µg/L), refers to the concentration of the ingredient in equilibrium with the condensed form—that is solid or liquid form—of this ingredient at a temperature of 25° C. and under a pressure of 1 atmosphere. It can be measured by using any of the known quantitative headspace analysis techniques in the art. A suitable method is described in Mueller and Lamparsky in Perfumes: Art, Science and Technology, Chapter 6 "The Measurement of Odors" at pages 176-179 (Elsevier 1991).

HS may be measured as follows: 500 mg of a test perfume ingredient is added to a headspace container which is then sealed. The container is then incubated at constant 25° C. until the ingredient reaches equilibrium between the gas and the liquid phase. A defined volume of this saturated headspace (usually 0.5-1.0 liter) is trapped on a micro filter using poly(4-ethyl styrene-co-divinyl benzene) porous material, for example Porapak® Q from Supelco, as sorbent. After filter extraction with an appropriate solvent (usually 30-100 microliters methyl tertiary butyl ether), an aliquot of the extract is analysed by GC. The concentration in the original headspace can be calculated (in terms of µg/L) from the headspace volume sucked through the micro filter and the aliquot of the filter extract injected into the gas chromatograph. The final headspace concentration value of a given test perfume ingredient is obtained as the mean value of three independent measurements each. Further information of the technique hereinabove described may be found in the article of Etzweiler, F.; Senn E. and Neuner-Jehle N., Ber. Bunsen-Ges. Phys. Chem. 1984, 88, 578-583, which is hereby incorporated by reference.

The term odour detection threshold (ODT) used herein above refers to the average concentration above which a perfume ingredient i can be perceived by a panellist and can be measured by olfactometry, as described, for example in Mueller and Lamparsky (op. cit). The Odour Detection Threshold (ODT) may be measured by using an olfactometer. The following steps can be carried out and the odour thresholds for each ingredient listed in Table 1 determined.

The olfactometer functions on the principle of a linear dilution of an ingredient in a carrier gas. The quantity of ingredient displaced depends on its vapour pressure and the carrier gas flow. A constant flow of nitrogen, regulated by a flow regulator, carries the ingredient from a sample container to a mixing chamber. There, the carrier gas-ingredient mixture is diluted with odourless air. From the mixing chamber one part of the diluted odorous air is allowed to flow via a fused silica capillary to the sniffing funnel. The flow rate through the capillary, which determines the dosage of odorous air from the mixing chamber into the sniffing funnel, depends on the opening the valve which can be regulated via PC from 1 to 256 ml in binary steps. The final dilution of the odorous air sample occurs in the glass funnel by flushing them permanently with odourless air at a flow rate of 8 L/min. Forced-choice triangle presentation is achieved by a special automated channel setting device where only one position of a switch the ingredient delivering capillary enters in the sniffing funnel, whereas in two other positions the capillary is positioned outside the funnel and where the effluent is sucked away. After each trial the channel setting is changed automatically and in a random order. The concentration is calculated from the ingredient vapour pressure and from the dilution ratios that were applied in the olfactometer, assuming that vapour pressure saturation is achieved in the sample generator. As a control the concentration is determined analytically by sampling a known volume from the capillary effluent into a headspace filter and by subsequent gas chromatographic quantitation of the ingredient in the desorption solution.

Each panellist (panel of 15 persons) starts sniffing at the olfactometer at a concentration level at which he perceives the ingredient at medium intensity. After three correct answers in three consecutive trials (or four correct answers of five trials) at the same level, stimulus concentration is decreased by a factor of two to the next lower level, and so on, until the panellist has reached his threshold level. The final threshold value of a given ingredient is obtained as the mean value of all individual threshold levels.

Reference herein to the wt % of a perfume ingredient in an encapsulated perfume composition is to be taken as reference to the concentration of a perfume ingredient or perfume ingredients based on the total amount of perfume ingredients contained in said encapsulated perfume composition. If an encapsulated perfume composition contains other non-perfume or technical ingredients, such as solvents, solubilizers, stabilizers, and the like, then the amount of these ingredients present is not to be taken into account when determining the wt % of perfume ingredients.

GROUP A perfume ingredients may be selected from the group consisting of decanal, undecanal, 2-methylundecanal (for example ALDEHYDE C 12 MNA PURE); dodecanal (for example ALDEHYDE C 12 LAURIC); tridecanal, tetradecanal, 3,7-dimethylocta-1,6-dien-3-ol (for example LINALOOL); (E)-3,7-dimethylnona-1,6-dien-3-ol (for example ETHYL LINALOOL); 3,7-dimethyloctan-3-ol (for example TETRAHYDRO LINALOOL); 2,6-dimethyloct-7-en-2-ol (for example DIHYDRO MYRCENOL); 2,6-dimethyloctan-2-ol (for example TETRAHYDRO MYRCENOL); (E)-4-methyldec-3-en-5-ol (for example UNDECAVERTOL); and the like.

In a preferred embodiment, GROUP A perfume ingredients typically includes ALDEHYDE C12; ALDEHYDE C12 MNA; LINALOOL; ETHYL LINALOOL; TETRA HYDRO LINALOOL; DIHYDROMYERCENOL; and TETRAHYDRO MYRCENOL.

GROUP B perfume ingredients may be selected from the group consisting of hexan-1-al (for example ALDEHYDE C 6 HEXYLIC FOOD GRADE, log(OV)=7.01); heptanal (for example ALDEHYDE C 7 HEPTYLIC, log(OV)=6.57); 2-(2-mercaptopropan-2-yl)-5-methylcyclohexanone (for example CORPS CASSIS, log(OV)=6.27); (E)-1-(2,6,6-trimethylcyclohexa-1,3-dien-1-yl)but-2-en-1-one (for example DAMASCENONE, log(OV)=7.34); (E)-1-(2,6,6-trimethylcyclohex-3-en-1-yl)but-2-en-1-one (for example DAMASCONE DELTA, log(OV)=7.6); (E)-dec-4-enal (for example DECENAL-4-TRANS, log(OV)=6.66); 1-methoxy-4-propylbenzene (for example DIHYDRO ANETHOLE, log(OV)=6.12); ethyl butanoate (for example ETHYL BUTYRATE, log(OV)=6.23); ethyl butanoate (for example ETHYL BUTYRATE, log(OV)=6.23); ethyl hexanoate (for example ETHYL CAPROATE, log(OV)=7.01); ethyl 2-methylpropionate (for example ETHYL ISOBUTYRATE, log(OV)=7.53); ethyl 3-methylbutanoate (for example ETHYL ISOVALERATE, log(OV)=8.4); ethyl 2-methylbutanoate (for example ETHYL METHYL-2-BUTYRATE, log(OV)=7.22); ethyl 2,6,6-trimethylcyclohexa-1,3-diene-1-carboxylate (for example ETHYL SAFRANATE, log(OV)=6.16); (1S,4S)-1,3,3-trimethyl-2-oxabicyclo[2.2.2]octane (for example EUCALYPTOL, log(OV)=7); methyl oct-2-ynoate (for example FOLIONE, log(OV)=6.04); 2-methoxyphenol (for example GUAIACOL, log(OV)=8); ethyl 2-methylpentanoate (for example MANZANATE, log(OV)=7.8); 2,6-dimethylhept-5-enal (for example MELONAL, log(OV)=6.57); methyl 2-hydroxy-5-methylbenzoate (for example METHYL CRESOTATE PARA, log(OV)=7.78); methyl 2-methylbutanoate (for example METHYL METHYL BUTYRATE, log(OV)=7.66); (2E,6Z)-nona-2,6-dienal (for example NONADIENAL, log(OV)=7.24); (2E,6Z)-nona-2,6-dien-1-ol (for example NONADIENOL-2,6, log(OV)=7.09); (Z)-non-6-enal (for example NONENAL-6-CIS, log(OV)=6.69); 2-phenyl-ethanal (for example PHENYL ACETALDEHYDE, log(OV)=6.86); (2E,5E)-5,6,7-trimethylocta-2,5-dien-4-one (for example POMAROSE, log(OV)=6.3); 4-methyl-2-(2-methylprop-1-en-1-yl)tetrahydro-2H-pyran (for example ROSE OXIDE CO, log(OV)=7.4); 2,6,6-trimethylcyclohexa-1,3-dienecarbaldehyde (for example SAFRANAL, log(OV)=6.24); 4-vinylcyclohex-1-enecarbaldehyde (for example SHISOLIA, log(OV)=6.51); 4-methylbenzaldehyde (for example TOLYL ALDEHYDE PARA EXTRA, log(OV)=6.22); 2-ethoxy-4-methylphenol (for example ULTRAVANIL, log(OV)=7.21); (3E,5Z)-undeca-1,3,5-triene (for example UNDECATRIENE, log(OV)=6.65); (2E,6Z)-nona-2,6-dienenitrile (for example VIOLET NITRILE, log(OV)=8.11); and ethyl cyclohexanecarboxylate (log(OV)=9.1).

In a preferred embodiment, GROUP B perfume ingredients include MANZANATE; DELTA DAMASCONE; DAMASCENONE; ETHYL METHYL-2-BUTYRATE; EUCALYPTOL; ETHYL CAPROATE; SHISOLIA; ETHYL BUTYRATE; ROSYRANE SUPER; ETHYL SAFRANATE; and ethyl cyclohexanecarboxylate. The encapsulated perfume composition may also comprise perfume ingredients that do not belong to GROUP A and GROUP B perfume ingredients, including 2,6,10-trimethylundec-9-enal (for example ADOXAL); 2-(tert-butyl)cyclohexyl acetate (for example AGRUMEX); allyl 2-(isopentyloxy)acetate (for example ALLYL AMYL GLYCOLATE); allyl 3-cyclohexylpropionate (for example ALLYL CYCLOHEXYL PROPIONATE); allyl heptanoate (for example ALLYL OENANTHATE); 1-((2-(tert-butyl)cyclohexyl)oxy)butan-2-ol (for example AMBER CORE); 1,3,4,5,6,7-hexahydro-.beta.1,1,5,5-pentamethyl-2H-2,4a-methanonaphthalene-8-ethanol (for example AMBERMAX); 3a,6,6,9a-tetramethyldodecahydronaphtho[2,1-b]furan (for example AMBROFIX); pentyl 2-hydroxybenzoate (for example AMYL SALICYLATE); 1-(3,3-dimethylcyclohexyl)ethyl formate (for example APHERMATE); (1R,2S,4R)-2'-isopropyl-1,7,7-trimethylspiro[bicyclo[2.2.1]heptane-2,4'[-1,3]dioxane] (for example BELAMBRE); (ethoxymethoxy)cyclododecane (for example BOISAMBRENE FORTE); (1S,2R,5R)-2-ethoxy-2,6,6-trimethyl-9-methylenebicyclo[3.3.1]nonane (for example BOISIRIS); (2S,4S)-1,7,7-trimethylbicyclo[2.2.1]heptan-2-yl acetate (for example BORNYL ACETATE); 1-butoxy-1-oxopropan-2-yl butanoate (for example BUTYL BUTYRO LACTATE); 4-(tert-butyl)cyclohexyl acetate (for example BUTYL CYCLOHEXYL ACETATE PARA); (Z)-4,11,11-trimethyl-8-methylenebicyclo[7.2.0]undec-4-ene (for example CARYOPHYLLENE); 1,1,2,3,3-pentamethyl-2,3,6,7-tetrahydro-1H-inden-4(5H)-one (for example CASHMERAN); 5-tert-butyl-2-methyl-5-propyl-2H-furan (for example CASSYRANE); (E)-3,7-dimethylocta-2,6-dienal (for example CITRAL LEMAROME N); 3,7-dimethyloct-6-enal (for example CITRONELLAL); 3,7-dimethyloct-6-en-1-ol (for example CITRONELLOL EXTRA); 3,7-dimethyloct-6-en-1-yl acetate (for example CITRONELLYL ACETATE); 3,7-dimethyloct-6-en-1-yl formate (for example CITRONELLYL FORMATE); 3,7-dimethyloct-6-enenitrile (for example CITRONELLYL NITRILE); 3,7-dimethyloct-6-en-1-yl propionate (for example CITRONELLYL PROPIONATE); dodecanenitrile (for example CLONAL); 4-cyclohexyl-2-methylbutan-2-ol (for example CORANOL); 3-(4-isopropylphenyl)-2-methylpropanal (for example CYCLAMEN ALDEHYDE); allyl 2-(cyclohexyloxy)acetate (for example CYCLOGALBANATE); cyclohexyl 2-hydroxybenzoate (for example CYCLOHEXYL SALICYLATE); (E)-1-(2,6,6-trimethylcyclohex-2-en-1-yl)but-2-en-1-one (for example DAMASCONE ALPHA); (E)-1-(2,6,6-trimethylcyclohex-1-en-1-yl)but-2-en-1-one (for example DAMASCONE BETA); 2-methyl-1-phenylpropan-2-ol (for example DIMETHYL BENZYL CARBINOL); 2-methyl-1-phenylpropan-2-yl acetate (for example DIMETHYL BENZYL CARBINYL ACETATE); 2-methyl-1-phenylpropan-2-yl butanoate (for example DIMETHYL bENZYL CARBINYL BUTYRATE); 4,7-dimethyloct-6-en-3-one (for example DIMETHYL OCTENONE); 2,6-dimethylheptan-2-ol (for example DIMETOL); 1-methyl-4-(prop-1-en-2-yl)cyclohex-1-ene (for example DIPENTENE); (E)-3-methyl-5-(2,2,3-trimethylcyclopent-3-en-1-yl)pent-4-en-2-ol (for example EBANOL); ethyl octanoate (for example ETHYL CAPRYLATE); ethyl heptanoate (for example ETHYL OENANTHATE); (2S)-1,3,3-trimethylbicyclo[2.2.1]heptan-2-yl acetate (for example FENCHYL ACETATE); (1S,2R,4R)-1,3,3-trimethylbicyclo[2.2.1]heptan-2-ol (for example FENCHYL ALCOHOL); 1-(3,5,5,6,8,8-hexamethyl-5,6,7,8-tetrahydronaphthalen-2-yl)ethanone (for example FIXOLIDE); 3-(4-ethylphenyl)-2,2-dimethylpropanal (for example FLORALOZONE); 3-(3-isopropylphenyl)butanal (for example FLORHYDRAL); (3aR,6S,7aS)-3a,4,5,6,7,7a-hexahydro-1H-4,7-methanoinden-6-yl propionate (for example FLOROCYCLENE); 2,4,6-trimethyl-4-phenyl-1,3-dioxane (for example FLOROPAL); 2-(sec-butyl)cyclohexanone (for example FRESKOMENTHE); (3aS,4S,7R,7aS)-ethyl octahydro-1H-4,7-methanoindene-3a-carboxylate (for example FRUITATE); 2-methyldecanenitrile (for example FRUTONILE); 4,6,6,7,8,8-hexamethyl-1,3,4,6,7,8-hexahydrocyclopenta[g]isochromene (for example GALAXOLIDE); 1-(3,3-dimethylcyclohex-1-en-1-yl)pent-4-en-1-one (for example GALBANONE PURE); (3aR,6S,7aS)-3a,4,5,6,7,7a-hexahydro-1H-4,7-methanoinden-6-yl isobutanoate (for example GARDOCYCLENE); (E)-3,7-dimethylocta-2,6-dien-1-ol (for example GERANIOL 980); (E)-3,7-dimethylocta-2,6-dien-1-yl acetate (for example GERANYL ACETATE); (E)-3,7-dimethylocta-2,6-dien-1-yl isobutanoate (for example GERANYL ISOBUTYRATE); ethyl 2-ethyl-6,6-dimethyl-cyclohex-2-enecarboxylate (for example GIVESCONE); (E)-oxacyclohexadec-12-en-2-one (for example HABANO-LIDE); methyl 3-oxo-2-pentylcyclopentaneacetate (for example HEDIONE); (2S)-ethyl 3-isopropylbicyclo[2.2.1]hept-5-ene-2-carboxylate (for example HERBANATE); (Z)-hex-3-en-1-yl butanoate (for example HEXENYL-3-CIS BUTYRATE); (E)-2-benzylideneoctanal (for example HEXYL CINNAMIC ALDEHYDE); hexyl 2-methylpropanoate (for example HEXYL ISOBUTYRATE); hexyl 2-hydroxybenzoate (for example HEXYL SALICYLATE); 4,4a,5,9b-tetrahydroindeno[1,2-d][1,3]dioxine (for example INDOFLOR); (E)-4-(2,6,6-trimethylcyclohex-1-en-1-yl)but-3-en-2-one (for example IONONE BETA); (E)-4-(2,6,6-trimethylcyclohex-2-en-1-yl)but-3-en-2-one (for example IRISONE ALPHA); (E)-4-(2,5,6,6-tetramethylcyclohex-2-en-1-yl)but-3-en-2-one (for example IRONE ALPHA); 1-(2,3,8,8-tetramethyl-1,2,3,4,5,6,7,8-octahydronaphthalen-2-yl)ethanone (for example ISO E SUPER); 2,4,6-trimethylcyclohex-3-enecarbaldehyde (for example ISOCYCLOCITRAL); isopropyl 2-methylbutanoate (for example ISOPROPYL METHYL-2-BUTYRATE); (E)-3-methyl-4-(2,6,6-trimethylcyclohex-2-en-1-yl)but-3-en-2-one (for example ISORALDEINE 70); (3aR,6S,7aS)-3a,4,5,6,7,7a-hexahydro-1H-4,7-methanoinden-6-yl acetate (for example JASMACYCLENE); (Z)-3-methyl-2-(pent-2-en-1-yl)cyclopent-2-enone (for example JASMONE CIS); 5-(sec-butyl)-2-(2,4-dimethylcyclohex-3-en-1-yl)-5-methyl-1,3-dioxane (for example KARANAL); (Z)-3,4,5,6,6-pentamethylhept-3-en-2-one (for example KOAVONE); (2E,6Z)-3,7-dimethylnona-2,6-dienenitrile (for example LEMONILE); (Z)-hex-3-en-1-yl methyl carbonate (for example LIFFAROME GIV); 3-(4-(tert-butyl)phenyl)-2-methylpropanal (for example LILIAL); 3,7-dimethylocta-1,6-dien-3-yl acetate (for example LINALYL ACETATE); 2-methyl-4-oxo-4H-pyran-3-yl isobutanoate (for example MALTYL ISOBUTYRATE); 2-isopropyl-5-methylcyclohexanol (for example MENTHOL NATURAL); 2-isopropyl-5-methylcyclohexanone (for example MENTHONE); 1-((1S,8aS)-1,4,4,6-tetramethyl-2,3,3a,4,5,8-hexahydro-1H-5,8a-methanoazulen-7-yl)ethanone (for example METHYL CEDRYL KETONE); undecan-2-one (for example METHYL NONYL KETONE); methyl non-2-ynoate (for example METHYL OCTYNE CARBONATE); 6,6-dimethoxy-2,5,5-trimethylhex-2-ene (for example METHYL PAMPLEMOUSSE); 4-(4-methylpent-3-en-1-yl)cyclohex-3-enecarbaldehyde (for example MYRALDENE); 2-(2-(4-methylcyclohex-3-en-1-yl)propyl)cyclopentanone (for example NECTARYL); (E)-methyl non-2-enoate (for example NEOFOLIONE); (Z)-3,7,11-trimethyldodeca-1,6,10-trien-3-yl acetate (for example NEROLIDYLE); (Z)-3,7-dimethylocta-2,6-dien-1-yl acetate (for example NERYL ACETATE); (2E,6Z)-nona-2,6-dien-1-ol (for example NONADIENOL-2,6, log(OV)=7.09); 3-(4-isobutyl-2-methylphenyl)propanal (for example NYMPHEAL); 4-(tert-pentyl)cyclohexanone (for example ORIVONE); 2-ethyl-N-methyl-N-(m-tolyl)butanamide (for example PARADISAMIDE); 2-cyclohexylidene-2-phenylacetonitrile (for example PEONILE); 2,2-dimethyl-2-pheylethyl propionate (for example PIVAROSE); 1-methyl-4-(4-methylpent-3-en-1-yl)cyclohex-3-enecarbaldehyde (for example PRECYCLEMONE b); 6-(sec-butyl)quinoline (for example PYRALONE); (E)-2-ethyl-4-(2,2,3-trimethylcyclopent-3-en-1-yl)but-2-en-1-ol (for example RADJANOL SUPER); 2,4-dimethyl-4-phenyltetrahydrofuran (for example RHUBAFURAN); 2,2,2-trichloro-1-phenylethyl acetate (for example ROSACETOL); dec-9-en-1-ol (for example ROSALVA); (1-methyl-2-(5-methylhex-4-en-2-yl)cyclopropyl)methanol (for example ROSYFOLIA); 1-(spiro[4.5]dec-6-en-7-yl)pent-4-en-1-one (for example SPIROGALBANONE PURE); (E)-5-methylheptan-3-one oxime (for example STEMONE); (E)-6-ethyl-3-methyloct-6-en-1-ol (for example SUPER MUGUET); (E)-2-((3,5-dimethylhex-3-en-2-yl)oxy)-2-methylpropyl cyclopropanecarboxylate (for example SYLKOLIDE); 1-methyl-4-propan-2-ylcyclohexa-1,4-diene (for example TERPINENE GAMMA); 1-methyl-4-(propan-2-ylidene)cyclohex-1-ene (for example TERPINOLENE); 2-(4-methylcyclohex-3-en-1-yl)propan-2-yl acetate (for example TERPINYL ACETATE); oxacyclohexadecan-2-one (for example THIBETOLIDE); (E)-tridec-2-enenitrile (for example TRIDECENE-2-NITRILE); 2,2,5-trimethyl-5-pentylcyclopentanone (for example VELOUTONE); (2,2-dimethoxyethyl)benzene (for example VIRIDINE); and the like; and mixture thereof.

Although it is preferred that the cores of core-shell microcapsules only contain perfume ingredients, it is contemplated that in addition to perfume ingredients, the contents of the cores may contain non-perfume ingredients or excipients such as solvents or diluents, which may be beneficial in reducing the amount of perfume composition that might leak from the cores. Such solvents are hydrophobic materials that are miscible in the perfume ingredients, and which have little or no odour in the quantities employed. Solvents commonly employed have high C log P values, for example greater than 6 and even greater than 10. Solvents include triglyceride oil, mono and diglycerides, mineral oil, silicone oil, diethyl phthalate, poly(alpha-olefins), castor oil and isopropyl myristate.

Microcapsules particularly suitable for use in the present invention have a shell comprising a thermosetting resin based on aminoplast chemistry. Such microcapsules are well known to the art and are obtained by interfacial polycondensation. Interfacial polycondensation involves forming a dispersion or emulsion of perfume droplets in an aqueous continuous phase containing a pre-condensate of polymeric materials under appropriate conditions of agitation to produce microcapsules of a desired size, and adjusting the reaction conditions to cause condensation of the pre-condensate by acid catalysis, resulting in the condensate separating from solution and surrounding the dispersed perfume droplets to produce a coherent film and the desired microcapsules. Polycondensation techniques are described, e. g. in U.S. Pat. Nos. 3,516,941, 4,520,142, 4,528,226, 4,681,806, 4,145,184 and GB 2 073 132 A, which are herein incorporated by reference.

Preferably, the microcapsules have a shell comprising an aminoplast terpolymer comprising polyol moieties, and especially aromatic polyol moieties, as described in WO 2008/098387 A1, which is herein incorporated by reference. Other aminoplast microcapsules that are particularly useful for the purpose of the invention are disclosed in co-pending applications PCT/EP2016/065538 and PCT/EP2016/064344, incorporated herein by reference.

An encapsulated perfume composition of the present invention may be prepared and presented in the form of a slurry, in which the microcapsules are dispersed in an aqueous suspending medium. If it is intended to present the encapsulated perfume composition in this form, the pH of the slurry may be adjusted to about 3 to 8 by the addition of a suitable acid, such as citric acid or formic acid and a preservative added.

Slurries of microcapsules will typically contain a suspending aid to ensure the microcapsules remain stably suspended and do not cream, form a sediment or otherwise agglomerate during storage. Suitable dispersing aids include pectin, alginate, arabinogalactan, carageenan, gellan gum, xanthan gum, guar gum, acrylates/acrylic polymers, water-swellable clays, fumed silicas, acrylate/aminoacrylate copolymers, and mixtures thereof. Preferred dispersants herein include those selected from the group consisting of acrylate/acrylic polymers, gellan gum, fumed silicas, acrylate/aminoacrylate copolymers, water-swellable clays, and mixtures thereof.

In order to prevent microbial contamination it is desirable that the microcapsule composition contains a preservative. The preservative may be contained in the core material and/or in the aqueous carrier. Suitable preservatives include quaternary compounds, biguanide compounds, and mixtures thereof.

In addition to any perfume composition that may be contained within the microcapsules, a slurry of microcapsules of the present invention may also contain free perfume in the suspending medium.

Alternatively, the encapsulated perfume composition, initially presented in the form of a slurry, may be dried to provide an encapsulated perfume composition in powder form. Drying may be carried out directly by spray drying or by fluid bed drying. Alternatively, the encapsulated perfume composition can be dried by decanting off the liquid from the slurry and drying the solids in an oven to produce a cake, which can then be rendered in powder form by a subsequent commination step.

Whatever means are employed to dry the encapsulated perfume composition, in order to prevent aggregation and improve the bulk flow properties of the microcapsules, it may be desirable to add a flow aid to the slurry before or after the drying process. Suitable flow aids will be known to the skilled person in the art and will include, without limitation silica, starch, calcium carbonate and sodium sulphate.

The size of the microcapsules employed in encapsulated perfume compositions according to the present invention can be adjusted as desired for use in any particular application.

In the context of the present invention, the mean diameter of the microcapsule is of from 5 to 50 µm, more preferably between 10 and 40 µm and most preferably between 15 and 25 µm.

The mean particle size can be determined in a manner known in the art. A particular method of measuring particle size is light scattering. Light scattering measurements can be made using a Malvern Mastersizer 2000S instrument and the Mie scattering theory. The principle of the Mie theory and how light scattering can be used to measure droplet size can be found, for example H. C. van de Hulst, Light scattering by small particles. Dover, New York, 1981. The primary information provided by static light scattering is the angular dependence of the light scattering intensity, which in turn is linked to the size and shape of the droplets However, in a standard operation method, the size of a sphere having a size equivalent to the size of the diffracting object, whatever the shape of this object, is calculated by the Malvern proprietary software provided with the apparatus. In case of polydisperse samples, the angular dependence of the overall scattering intensity contains information about the size distribution in the sample. The output is a histogram representing the total volume of droplets belonging to a given size class as a function of the capsule size, whereas an arbitrary number of 50 size classes can be chosen.

Experimentally, a few drops of slurry are added to a circulating stream of degased water flowing through a scattering cell. The angular distribution of the scattering intensity is measured and analyzed by Malvern proprietary software to provide the average size and size-distribution of the droplets present in the sample. In the case of an unimodal (monodisperse) droplet distribution the percentiles Dv 10, Dv 50 and Dv 90 are used as characteristics of the droplets size distribution, whereas Dv 50 corresponds to the median of the distribution and is taken as a measure of the mean diameter of the microcapsules.

The shell thickness may be calculated straightforwardly from the weight and density of the shell material in the slurry, the weight and density of the core material in the slurry, and the average size of the microcapsules.

In the context of the present invention, the calculated shell thickness may be obtained by considering that the shell and core material densities are equal and assuming all microcapsules have virtually the same size as the median of the size distribution. Equation 1 is used to calculate the shell thickness h, according the the present invention, with $r_{capsule}$ being the median microcapsule radius, $r_{core}$, the unknown median core radius, $w_{core}$ being the weight of the core material in the slurry, $w_{shell}$ being the weight of the shell material in the slurry.

$$h=(r_{capsule}-r_{core})=[1-(w_{core}/(w_{shell}+w_{core}))^{1/3}]r_{capsule}$$

Hence, for the purpose of the present invention, the core to shell weight ratio of the microcapsules is preferably about 90:10 at least, or more particularly 95:5 at least.

Consumer products that are considered to be especially extractive in the context of the present invention are products containing un-structured surfactants. Un-structured surfactants are relatively free to extract perfume ingredients by forming micelles or vesicles around them, and solubilize them. They can be contrasted with "structured surfactants", which are essentially immobilized in a structure, such as a liquid crystalline, generally lamellar phase (sometimes called "mesophases") and are thus generally unavailable to form micelles or vesicles, and are far less aggressive or extractive as a result. Un-structured surfactants comprising alkylene oxide moieties, and especially ethylene oxide moieties, such as fatty alcohol ethoxylates, are particularly prone to extract encapsulated perfume compositions and to provoke extensive microcapsule leakage over time.

Typical consumer products concerned by the present invention include laundry care detergents, laundry care conditioners, fabric refreshers, personal care cleansing compositions, such as shampoos, bath and shower gels, liquid soaps, soap bars and the like, personal care conditioning composition, such as hair care conditioners, bath and shower lotions, deodorant compositions, antiperspirant compositions, home care compositions, such as hard surface cleaners, heavy duty detergents and the like.

In many cases, and especially in the laundry care, personal care and home care categories, the consumer products concerned by the present invention contain surfactants.

In a particular embodiment of the present invention there is provided a consumer product comprising a compacted perfume composition and at least one surfactant, selected from anionic, cationic, amphoteric or non-ionic surfactants. Typical anionic surfactants include but are not limited to sodium lauryl sulfate, sodium laureth sulfate, sodium trideceth sulfate, ammonium lauryl sulphate, ammonium laureth sulphate, potassium laureth sulfate, sodium tridecyl benzene sulfonate, sodium dodecyl benzene sulfonate, sodium xylene sulfonate, monoethanolamine lauryl sulfate, monoethanolamine laureth sulfate, triethanolamine lauryl sulfate, triethanolamine laureth sulfate, lauryl sarcosine, cocoyl sarcosine, sodium lauryl sarcosinate, sodium lauroyl sarcosinate, triethylamine lauryl sulfate, triethylamine laureth sulfate, diethanolamine lauryl sulfate, diethanolamine laureth sulfate, lauric monoglyceride sodium sulfate, ammonium cocoyl sulfate, ammonium lauroyl sulfate, sodium cocoyl sulfate, sodium lauroyl sulfate, sodium cocoyl isethionate, potassium cocoyl sulfate, potassium lauryl sulfate, monoethanolamine cocoyl sulfate, monoetha nolamine lauryl sulfate, triethanolamine lauryl sulfate, sodium hydroxyethyl-2-decyl ether sulfates, sodium methyl-2-hydroxydecyl ether sulfates, sodium hydroxyethyl-2-dodecyl ether sulfates, sodium monoethoxylated lauryl alkyl sulfates, C12-C18 alkyl sulfonates, ethoxylated or native linear and ramified C12-C18 alcohol sulfates, ethoxylated or native linear and ramified C12-C18 alcohol sulfates, and mixtures thereof.

Typical cationic surfactants include but are not limited to quaternary ammonium salts having one or two alkyl chain comprising 10 to 22 carbon atoms, and optionally hydroxyl groups, and two to three alkyl groups having 1 to 4 carbon or hydroxyalkyl or hydroxyl groups, or alkoxy groups, having typically about 1 to about 10 ethylene oxide moieties, and an anion selected from the group of halides, hydroxides, acetates and methylsulfate, such as ditallowalkyldimethyl (or diethyl or dihydroxyethyl) ammonium chloride, ditallowalkyldimethylammonium methyl sulfate, methyl tallowalkyl amido ethyl, ditallowalkyldimethylammonium methyl sulfate, dihexadecylalkyl dimethyl (or diethyl, or dihydroxyethyl) ammonium chloride, dioctadecyl-alkyl dimethylammonium chloride, such as DODMAC (dioctadecyl dimethyl ammonium chloride), and dieicosylalkyl dimethylammonium chloride, ethyl-tallowalkyl imidazolinium methyl sulphate, ditallowalkyldimethylammonium methyl sulfate, methyl tallowalkyl amido ethyl tallowalkyl imidazolinium methyl sulfate, quaternary ammonium salts having one or two acyloxy-alkyl chains, one or two alkyl groups and/or one or two hydroxyalkyl groups, such as so-called esterquat (N-methyl-N,N,bis[2-(C16-C18-acetoxy)ethyl)]-N-(2-hydroxyethyl) ammonium methosulfate), diesterquat (N,N,N-trimethyl-N-[1,2-di-(C16-C18-acyloxy)propyl ammonium salts), DEEDMAC (N,N-dimethyl-N,N-bis([2-(-[(1-oxooctadecyl)oxy]ethyl) ammonium chloride, HEQ (N,N,N-trimethyl-N-[(Z)-2-hydroxy-3-[(1-oxo-octadec-9-enyl)oxy]] ammonium chloride, TEAQ (diquaternized methylsulfate salt of the reaction product between C10-C20 saturated and unsaturated fatty acids and triethanoloamine), alkylbenzyl dialkyl ammonium chloride, whereas the anion is selected from halides (such as chloride or bromide), hydroxy, ethylsulfate, acetate, carbonate, nitrate, phosphate and methylcarbonate.

Typical cationogenic surfactants include but are not limited to primary, secondary and tertiary amines, and ethoxylated fatty amines, such as lauriminopropyldimethyl amine, lauriminoethyldimethyl amine, myristyl amine, tridecyl amine, N-oleyl-1,3-propane diamine, ethoxylated N-tallow-1,3-propanediamine.

Typical zwitterionic surfactants include but are not limited to derivatives of aliphatic quaternary ammonium, phosphonium, and sulfonium compounds having linear or ramified alkyl, or alkenyl, or hydroxyl alkyl or alkoxy radicals, one of which having from about 8 to about 18 carbon atoms and another of which containing an anionic group selected from carboxyl, sulfonate, sulfate, succinate, phosphate or phosphonate groups. The alkoxy radicals include typically about 1 to about 10 ethylene oxide moieties or about 1 to about 3 glyceryl moieties. The hydroxyl alkyl radicals comprise typically alkylol moieties having 1 to 3 carbon atoms. A particular class of zwitterionic surfactant includes betaines comprising a quaternized cationic ammonium group and an anionic carboxylate group, separated by at least one methylene group, such as coco dimethylcarboxymethyl betaine, lauryl dimethyl carboxymethyl betaine, lauryl dimethyl alpha-carboxyethyl betaine, cetyl dimethyl carboxymethyl betaine, oleyl dimethyl gamma-carboxypropyl betaine, lauryl and stearyl bis-(2-hydroxyethyl) carboxymethyl betaine, oleyl dimethyl gamma-carboxypropyl betaine, and lauryl bis-(2-hydroxypropyl)-alpha-carboxyethyl betaine. Other betaines include amidoalkyl, sulfoalkyl and alkyl amidosufo betaines, wherein the alkyl moiety is typically an ethyl or a propyl moiety, such as cocoamidopropyl betaine, cocodimethylsulfopropyl betaine, lauryl dimethyl sulfoethyl betaine, lauryl bis-(2-hydroxyethyl) sulfopropyl betaine and the like.

Typical amphoteric surfactants include but are not limited to derivatives of primary, secondary and tertiary amines having linear or ramified alkyl or alkenyl radicals, one of which having from about 8 to about 18 carbon atoms and another of which containing an anionic group selected from carboxyl, sulfonate, sulfate, succinate, phosphate or phosphonate groups, such as sodium 3-dodecylimino propionate, sodium 3-dodecyliminopropane sulfonate.

Non-ionic surfactants include but are not limited to C4-C22 alkyl ethoxylates with about 1-25 ethylene oxide units, including the so-called narrow peaked alkyl ethoxylates, particularly ethoxylates and mixed ethoxylates/propoxylates, alkyl dialkyl amine oxides, alkyl polyglycosides, alkanoyl glucose amides, and mixtures thereof. Specific examples of non-ionic surfactants are the condensation products of aliphatic alcohols with from about 1 to about 22 moles of ethylene oxide. The alkyl chain of the aliphatic alcohol can either be straight or branched, primary or secondary, and generally contains from about 8 to about 18 carbon atoms, preferably C8 to C18 (e.g. C10) with 2 to 14 moles of ethylene oxide, such as the condensation product of C11-C15 linear secondary alcohol with 9 moles ethylene oxide, or the condensation product of C12-C14 primary alcohol with 6 moles ethylene oxide, or the condensation product of C14-C15 linear alcohol with 4 moles of ethylene oxide, or the condensation product of C13-C15 alcohol with 9 moles ethylene, or the condensation products of C13 alcohols and 2-21 moles of ethylene oxide. This category of non-ionic surfactant is referred to generally as "alkyl ethoxylates."

Other examples of non-ionic surfactants include the condensation products of ethylene oxide with a hydrophobic base formed by the condensation of propylene oxide with propylene glycol (e.g. PPG-1-PEG-9 Lauryl Glycol Ether).

Further examples of non-ionic surfactants are the polyethylene glycol sorbitol ethers containing 3-30 EO units (including, for example, sorbitol esters with oleic, myristic, stearic, palmitic acid, and the like).

Further examples of non-ionic surfactants are the condensation products of ethylene oxide (EO) with the product resulting from the reaction of propylene oxide and ethylene diamine.

Semi-polar non-ionic surfactants are a special category of non-ionic surfactants which include water-soluble amine oxides. These amine oxide surfactants in particular include C10-C18 alkyl dimethyl amine oxides and C8-C12 alkoxy ethyl dihydroxy ethyl amine oxides, such as NN-dihydroxy-ethyl-N-stearamine oxide, ethoxylated lauramide and lauryldimethylamine oxide.

Other non-ionic surfactants are alkyl polyglycosides including, for example, C8-C10 polyglycosides, such as C12-C16 alkyl polyglycosides, C8-C16 alkyl polyglycosides, C5 Amyl xyloside) and mixture of C5 Amyl, C8 Capryl, C12 Lauryl. The term "alkyl" as used hereinabove for the non-ionic sugar-based surfactant refers to saturated linear alkyl residues having 3 to 21 carbon atoms, including hexyl, octyl, decanyl, dodecanyl, tetradecanyl, hexadecanyl, and octadecanyl.

Further non-ionic surfactants include, for example, PEG 40 or PEG 400 hydrogenated castor oil.

Further non-ionic surfactants include glycerol-based surfactants having alkyl, alkenyl or hydroxyalkenyl residues having 5 to 21 carbon atoms, and different numbers of glyceryl moieties, such as octanoic acid hexaglyceryl ester, decanoic acid tetraglyceryl ester, riccinoleic acid hexaglyceryl ester, cocoic acids tetraglyceryl esters, and mixture thereof.

The consumer products concerned by the present invention may include acids or bases, or substances providing acidity or alkalinity, also referred to as acidity sources or alkalinity sources. The acids or acidity sources may be inorganic or organic. Inorganic acids and acidity sources may include hydrochloric acid, sulfuric acid, sulfamic acid, phosphoric acids and the like. Organic acids or acidity sources may include benzoic acid, citric acid, malic acid, and the like. The bases or alkalinity sources may also be inorganic or organic. Inorganic bases and alkalinity sources may include sodium hydroxide, ammonia, and salts comprising carbonates, phosphates, and the like.

The consumer products concerned by the present invention may include builders for reducing water hardness, such as phosphates, polyphosphates, polycarboxylates, sodium citrate, sodium carbonate, sodium silicate, sodium aluminosilicate (zeolite), and the like.

In many cases, the consumer products concerned by the present invention are liquid and may include further additives, such as solvents, fillers, texturing agents, such as thickener and rheological aids, distributing aids, anti-redeposition agents, preservative agents, deodorizing agents, cosmetic active ingredients, surface enhancing agents, In a particular embodiment of the present invention is provided a consumer product comprising microcapsules of the present invention and at least one solvent selected from water-soluble solvents, or water-insoluble, or partially water-soluble solvents.

Water-soluble co-solvents include, but are not limited to, ethanol, 1-propanol, 2-propanol, 1-butanol, 1,2-propane diol, 1,3-propane diol, 1,2-butanediol, 1,2-pentandiol 1,2-hexanediol, 1,2-heptanediol, 2-methyl-pentan-2,4-diol, carbitol, glycol ethers, such as propylene glycol, dipropylene glycol, 1,3-propanediol, glycol esters and glycol ethers, such as dipropylene glycol methyl ether acetate, dipropylene glycol methyl ether, propylene glycol n-butyl ether, diethylene glycol butyl ether, hexylene glycol, methyl methoxy butanol, (+/−)-2,2-dimethyl-4-hydroxymethyl-1,3-dioxolane, glycerine, dimethyl isosorbide, triethyl citrate and mixtures thereof.

Water-insoluble or partially insoluble solvents include, but are not limited to, isopropyl myristate, methyl myristate, alkyl esters, such as methyl linoleate, methyl palmitate, ethyl laurate, ethyl linoleate, ethyl oleate, ethyl octanoate, dibenzyl ether and diethyl phtalate, dibasic ester DBE (blend composed of diisobutyl glutarate, diisobutyl succinate, and diisobutyl adipate, commercially available from Solvay, or blend composed of diisobutyl glutarate, and diisobutyl adipate, commercially available from Invista, and hydrocarbons.

In a particular embodiment of the present invention there is provided a consumer product comprising microcapsules of the present invention and at least one texturing agent and/or colloid stabilizer, selected from rheology modifiers, thickener, gel-forming agents, thixotropic agents, and dispersing agents.

These texturing agents and/or colloid stabilizers are typically water soluble of partially water soluble, or surface active polymers. These polymers include, but are not limited to quaternized hydroxyethyl cellulose, poly(diallyl ammonium chloride-co-acrylamide), quaternized guar gum, poly(acrylamidopropyltrimethyl ammonium chloride-co-acrylamide) copolymers, poly(methacrylamidopropyltrimethyl ammonium chloride), polyethyleneimine, poly[(3-methyl-1-vinylimidazolium methyl sulfate)-co-(1-vinylpyrrolidone, cationic polyamines, cationic polyacrylamide, poly(trimethylaminoethyl methacrylate), poyl(vinylamine, poly(dimethyldiallyl ammonium chloride), also called poly(DADMAC), chitosan, carboxymethyl cellulose, xanthan gum, acacia gum, ghatti gum, tragaganth gum, Arabic gum, sodium alginate, ethoxylated alginate, gelatine, dextran, hydroxythyl cellulose, hydroxypropyl cellulose, hydroxypropyl methylcellulose, poly(ethylene oxide), poly(ethylene oxide-b-propylene oxide) block-copolymers, polyacrylamide, polyacrylic acid or carbomers, sodium polyacrylate, acrylates copolymer, acrylates crosspolymer-4, acrylates crosspolymer-3, polyacrylate-2 crosspolymer, and polyacrylate-14, crosslinked acrylates/C10-30 alkyl acrylate copolymers, polyvinyl alcohol, polyvinyl pyrrolidone, pectin, and modified.

In a particular embodiment of the present invention is provided a consumer product, for example a hair care product, comprising microcapsules of the present invention and at least one silicone, selected from, but not limited to dimethicone, poly(dimethylsiloxabedimethylsiloxane), amino-silicone, such as amodimethiocone, trialkylammonium-silicone salts, ethoxylated silicones and the like.

In a particular embodiment of the present invention is provided a consumer product comprising microcapsules of the present invention and at least one active cosmetic ingredient selected from, but not limited to emollients, moisturizing agents, anti-wrinkle agents, exfoliating agents, sunscreen agents, dyes, pigments, talcum, conditioning agents, hair styling agents, and antidandruff agents. In a particular embodiment of the present invention is provided a consumer product comprising microcapsules of the present invention and at least one fabric enhancing agent, selected from, but not limited to softening agents, optical brighteners and antistatic agents.

In a particular embodiment of the present invention is provided a consumer product comprising a compacted perfume composition and at least one deodorizing agent selected from, but not limited to zinc derivatives, essential oils, sodium undecylenate, methyl undecylenate, 2-hydroxypropyl beta cyclodextrin, soyethyl morpholinium ethosulfate, crotonates and fumarates, and alkylene carbonates.

In a particular embodiment of the present invention is provided a consumer product, for example home care products, comprising the compacted perfume composition and at least one solubilized, water soluble uncomplexed cyclodextrin selected from, but not limited to alpha-cyclodextrin, beta-cyclodextrin, gamma cyclodextrin and/or their derivatives, and/or mixture thereof. Cyclodextrin derivatives include, but are not limited to methoxy, ethoxy cyclodextrins, hydroxyl ethyl cyclodextrins, hydroxypropyl cyclodextrins, cationic cyclodextrins, such as 2-hydroxy-3-(trimethylammonium) propyloxy cyclodextrins, anionic cyclodextrins, such as carboxymethyl cyclodextrins and cyclodextrin sulfates and the like.

In a particular embodiment of the present invention is provided a consumer product, for example an antiperspirant comprising aluminium chlorohydrates, aluminium zirconium tetrachlorohydrex glycin complex, and the like.

In a particular embodiment of the present invention is provided a consumer product comprising microcapsules of the present invention and at least one preservative selected from, but not limited to butylated hydroxyanisole (BHA), butylated hydroxytoluene (BHT), dilauryl thiodipropionate, alkyl parabene, tocopherols and the like. In another embodiment, a suitable preservative includes a combination of benzisothiazolone (BIT), methylisothiazolone (MIT) and/or laurylamine dipropylenediamine (BDA), and mixtures thereof, and mixtures of NN'-dihydroxymethyl urea and 1,6-dihydroxy-2,5-dioxo-hexane.

The invention will be further described, by way of illustration, in the following examples.

EXAMPLE 1

Microcapsules were prepared according to the method set forth in WO/2008/098387, example 1.3, sample P5.2, using different perfumes having variable combinations of GROUP A ingredients, long chain saturated, alkyl aldehydes and tertiary diterpenic alcohols and tertiary diterpenic alcohol derivatives. The solid content of the capsule slurries was 40±2 wt %, wherein "solid content" refers to the percentage by weight of perfume-containing microcapsules in the slurry. In each case, an amount of slurry equivalent to 0.2 wt % of microcapsules was added to a fabric care softener composition having the formula described in Table 1.2. The softener composition containing the microcapsules was stored one month at 37° C. before use.

20 ml of aged softener containing 0.5 wt % microcapsules were added to 1 kg of terry towelling during a rinse cycle performed in a wash machine having a capacity of 15 litres. The towels were carefully removed from the wash machine and olfactive assessment was performed by sniffing the wet towels, without handling them with hands or any other instrument. The assessment was performed by a panel of 5 trained panellists. The smell was scored according to the following scale: 1=barely noticeable, 2=weak, 3=medium, 4=strong and 5=very strong. Decimal scoring was allowed. The results were the analysed using a binary scale: all samples having a score lower than 3.5 were attributed a "NP" (not performing) binary score and all samples having a score equal to or higher than 3.5 were attributed a "P" (performing) binary score. Both composition data and evaluation binary scores are reported in Table 1.

TABLE 1

Composition and pre-rub performance of encapsulated perfumes

| Ingredient | Perfume | | | | | | | | |
|---|---|---|---|---|---|---|---|---|---|
| | A | B | C | D | E | F | G | H | I |
| TETRAHYDROLINALOOL | | | 35 | 10 | 17 | | 10 | | 15 |
| LINALOL SYNT | | | | | | 10 | | | |
| UNDECAVERTOL | | | | | | | 9 | | 2 |
| ALDEHYDE C12 MNA & C12 | | | | 8 | | | 2 | 5 | |
| SUM OF GROUP A INGREDIENTS | 0 | 0 | 35 | 35 | 17 | 10 | 21 | 5 | 17 |
| EUCALYPTOL COSMOS | 12 | 12 | | 2 | 12 | | | 12 | |
| MANZANATE | | 3 | | | | | 2 | | 3 |
| ETHYL 2-METHYLBUTYRATE | | | | | | | 2 | | 2 |
| DAMASCENONE | | | | | | 15 | | | |
| DAMASCONE DELTA | 12 | | | | 2 | | 2 | 6 | |
| SUM OF GROUP B INGREDIENTS | 24 | 15 | 0 | 2 | 14 | 15 | 6 | 18 | 5 |
| HEDIONE | 28 | | 4.4 | | 20 | | | | |
| CYCLIC AND AROMATIC ESTERS | | 4 | 6 | 2 | | 40.6 | | | 2 |
| NITRILES | | | | 5 | | | | | |
| CYCLENES | 17 | 35 | 15.8 | 8 | 15 | | 14 | 17 | 10 |
| SALICYCATES | 14 | | | 2 | 20 | | 10 | 18.5 | |
| CYCLIC KETONES | | | | 26 | | 15 | 1.5 | 3 | 4 |
| AGRUMEX | 10 | 37.7 | 20 | | 7 | | 12 | 7 | 20 |
| LACTONES | | | | 4 | | 15 | 11 | | 10 |
| ALLYL ESTERS | | | | | | | 8.2 | | 7.3 |
| OTHER ALKYL ESTERS | | | 9.4 | 4 | | 3 | 9 | 23 | 19.3 |
| YARA YARA | 2 | | | | 2 | | | | |
| OTHER ALDEHYDES | 1 | 5 | 9.4 | 19.5 | 3.5 | | 3 | 1.5 | 2 |
| EBANOL OR JAVANOL | 1 | | | | 1 | 1 | | | |
| CITRUS OILS | | 3 | | 5 | | | | 3 | |
| MINOR COMPONENTS | 3 | 0.3 | | 4.5 | 0.5 | 0.4 | 4.3 | 4 | 3.4 |
| SUM OF ALL INGREDIENTS (1) | 100 | 100 | 100 | 100 | 100 | 100 | 100 | 100 | 100 |
| Pre-rub performance | NP | NP | NP | NP | P | P | P | P | P |

The results confirm the importance of the synergies between the saturated alkyl aldehydes and di-terpenic alcohols of GROUP A on one hand and the GROUP B ingredients on the other hand on the pre-rub performances of the microcapsules. If none of the alkyl aldehydes and/or terpenols is present in the composition, the pre-rub performance is insufficient, even if significant amount of GROUP B ingredients are used in the composition. Conversely, if none of the perfume ingredients of GROUP B is present in the composition, or if these are used in insufficient amounts, the pre-rub performance is insufficient, even if significant amount of GROUP A ingredients are used in the composition.

The invention claimed is:

1. An encapsulated perfume composition, comprising a plurality of core-shell microcapsules and wherein:
   a. the microcapsule shell comprises an aminoplast resin which has a calculated shell thickness lower than 0.5 μm; and
   b. the perfume composition which is encapsulated within the microcapsules comprises:
      i. from 5 to 30% by weight of GROUP A perfume ingredients being one or more perfume ingredients selected from the group consisting of: long chain aldehydes having at least 11 carbon atoms; and, tertiary alcohols having at least 10 carbon atoms; and,
      ii. from 5 to 25% by weight of GROUP B blooming perfume ingredients being one or more perfume ingredients selected from the group consisting of: hexanal; heptanal; 2-(2-mercaptopropan-2-yl)-5-methylcyclohexanone; (E)-1-(2,6,6-trimethylcyclohexa-1,3-dien-1-yl)but-2-en-1-one; (E)-1-(2,6,6-trimethylcyclohex-3-en-1-yl)but-2-en-1-one; (E)-dec-4-enal; 1-methoxy-4-propylbenzene; ethyl butanoate; ethyl hexanoate; ethyl 2-methylpropionate; ethyl 3-methylbutanoate; ethyl 2-methylbutanoate; ethyl 2,6,6-trimethylcyclohexa-1,3-diene-1-carboxylate; (1s,4s)-1,3,3-trimethyl-2-oxabicyclo[2.2.2] octane; methyl oct-2-ynoate; 2-methoxyphenol; ethyl 2-methylpentanoate; 2,6-dimethylhept-5-enal; methyl 2-hydroxy-5-methylbenzoate; methyl 2-methylbutanoate; (2E,6Z)-nona-2,6-dienal; (2E,6Z)-nona-2,6-dien-1-ol; (Z)-non-6-enal; 2-phenylethanal; (2E,5E)-5,6,7-trimethylocta-2,5-dien-4-one; 4-methyl-2-(2-methylprop-1-en-1-yl)tetrahydro-2H-pyran; 2,6,6-trimethylcyclohexa-1,3-dienecarbaldehyde; 4-vinylcyclohex-1-enecarbaldehyde; 4-methylbenzaldehyde; 2-ethoxy-4-methylphenol; (3E,5Z)-undeca-1,3,5-triene; (2E,6Z)-nona-2,6-dienenitrile; and ethyl cyclohexanecarboxylate;
   wherein, in the encapsulated perfume composition, the GROUP A perfume ingredients and the GROUP B blooming perfume ingredients are present in the relative concentration ranges such that:
      when the level of GROUP A perfume ingredients is from 5 to 10 wt %, then the level of GROUP B blooming perfume ingredients must be from 10 to 25 wt %;
      when the level of GROUP A perfume ingredients is from 10 to 30 wt %, then the level of GROUP B blooming perfume ingredients must be from 5 to 25 wt %;
      when the level of GROUP B blooming perfume ingredients is from 5 to 10 wt %, then the level of GROUP A perfume ingredients must be from 10 to 30 wt %; and,
      when the level of GROUP B blooming perfume ingredients is from 10 to 25 wt %, then the level of GROUP A perfume ingredients must be from 5 to 30 wt %;
   wherein the core to shell weight ratio of the microcapsules is about 90:10;
   and wherein the core-shell microcapsules are dispersed in an aqueous dispersing medium in a form of a slurry and wherein the slurry is stable and pourable.

2. The encapsulated perfume composition according to claim 1, wherein the at GROUP A perfume ingredients are selected from the group consisting of: undecanal, 2-methylundecanal, dodecanal, tridecanal, tetradecanal, 3,7-dimethylocta-1,6-dien-3-ol, (E)-3,7-dimethylnona-1,6-dien-3-ol, 3,7-dimethyloctan-3-ol, 2,6-dimethyloct-7-en-2-ol, 2,6-dimethyloctan-2-ol, and (E)-4-methyldec-3-en-5-ol.

3. A consumer product comprising an encapsulated perfume composition according to claim 1.

4. The consumer product according to claim 3, which is a rinse-off home care or is a personal care product.

5. A rinse-off product according to claim 4, which is a cleaning product selected from the group consisting of: a detergent, a shampoo, a soap or a cleansing composition.

6. The rinse-off product according to claim 4, which is a fabric care conditioner or is a hair care conditioner.

7. The consumer product according to claim 4, which is a leave-on personal care product.

8. The leave-on product according to claim 7 which is a deodorant product.

9. The leave on product according to claim 7 which is an anti-perspirant product.

10. The encapsulated perfume composition according to claim 1, providing enhanced pre-rub performance.

11. An encapsulated perfume composition comprising a plurality of core-shell microcapsules and wherein:
    a. the microcapsule shell comprises an aminoplast resin and has a calculated shell thickness lower than 0.5 μm; and
    b. the perfume composition which is encapsulated within the microcapsules comprises:
       i. from 5 to 30% by weight of GROUP A perfume ingredients being one or more perfume ingredients selected from the group consisting of: undecanal, 2-methylundecanal, dodecanal, tridecanal, 3,7-dimethylocat-1,6-dien-3-ol, (E)-3,7-diemethylnona-1,6-dien-3-ol, 3,7-dimethyloctan-3-ol, 2,6-dimethyloct-7-en-2-ol, 2,6-dimethyloctan-2-ol, and (E)-4-methyldec-3-en-5-ol and,
       ii. from 5 to 25% by weight of GROUP B blooming perfume ingredients being one or more perfume ingredients selected from the group consisting of: hexanal; heptanal; 2-(2-mercaptopropan-2-yl)-5-methylcyclohexanone; (E)-1-(2,6,6-trimethylcyclohexa-1,3-dien-1-yl) but-2-en-1-one; (E)-1-(2,6,6-trimethylcyclohex-3-en-1-yl) but-2-en-1-one; (E)-dec-4-enal; 1-methoxy-4-propylbenzene; ethyl butanoate; ethyl hexanoate; ethyl 2-methylpropionate; ethyl 3-methylbutanoate; ethyl 2,6,6-trimethylcyclohexa-1,3-diene-1-carboxylate; (1s,4s)-1,3,3-trimethyl-2-oxabicyclo [2.2.2]octane; methyl oct-2-ynoate; 2-methoxyphenol; ethyl 2-methylpentanoate; 2,6-dimethylhept-5-enal; methyl 2-hydroxy-5-methylbenzoate; methyl 2-methylbutanoate; (2E,6Z)-nona-2,6-dienal; (2E,6Z)-nona-2,6-dien-1-ol; (Z)-non-6-enal; 2-phenylethanal; (2E,5E)-5,6,7-trimethylocta-2,5-dien-4-one; 4-methyl-2-(2-methylprop-1-en-1-yl)tetrahydro-2H-pyran; 2,6,6-trimethylcyclohexa-1,3- dienecarbaldehyde; 4-vinylcyclohex-1-enecarbaldehyde; 4-methylbenzaldehyde; 2-ethoxy-4-methylphenol; (3E,5Z)-undeca-1,3,5-triene; (2E,6Z)-nona-2,6-dienenitrile; and ethyl cyclohexanecarboxylate;

wherein, in the encapsulated perfume composition, the GROUP A perfume ingredients and the GROUP B blooming perfume ingredients are present in the relative concentration ranges such that:

when the level of GROUP A perfume ingredients is from 5 to 10 wt %, then the level of GROUP B blooming perfume ingredients must be from 10 to 25 wt %;

when the level of GROUP A perfume ingredients is from 10 to 30 wt %, then the level of GROUP B blooming perfume ingredients must be from 5 to 25 wt %;

when the level of GROUP B blooming perfume ingredients is from 5 to 10 wt %, then the level of GROUP A perfume ingredients must be from 10 to 30 wt %; and, when the level of GROUP B blooming perfume ingredients is from 10 to 25 wt %, then the level of GROUP A perfume ingredients must be from 5 to 30 wt %;

wherein the core to shell weight ratio of the microcapsules is about 90:10;

and wherein the core-shell microcapsules are dispersed in an aqueous dispersing medium in the form of a slurry, and wherein the slurry is stable and pourable.

12. The encapsulated perfume composition according to claim 11, wherein the GROUP A perfume ingredients are selected from the group consisting of: 2-methylundecanal, dodecanal, 3,7-dimethylocta-1,6-dien-3-ol and 3,7-dimethyloctan-3-ol.

13. The encapsulated perfume composition according to claim 11, wherein the GROUP B perfume ingredients are selected from the group consisting of: (E)-1-(2,6,6-trimethylcyclohexa-1,3-dien-1-yl) but-2-en-1-one; (E)-1-(2,6,6-trimethylcyclohex-3-en-1-yl) but-2-en-1-one and (1s,4s)-1,3,3-trimethyl-2-oxabicyclo [2.2.2] octane.

14. The encapsulated perfume composition according to claim 11, providing enhanced pre-rub performance.

15. A consumer product comprising an encapsulated perfume composition according to claim 11.

16. The consumer product according to claim 11, which is a rinse-off home care or is a personal care product.

17. The rinse-off product according to claim 16, which is a fabric care conditioner or is a hair care conditioner.

* * * * *